United States Patent [19]

Parisi

[11] Patent Number: 4,838,853
[45] Date of Patent: Jun. 13, 1989

[54] APPARATUS FOR TRIMMING MENISCUS
[75] Inventor: Tulio T. Parisi, San Diego, Calif.
[73] Assignee: InterVentional Technologies Inc., San Diego, Calif.
[21] Appl. No.: 10,999
[22] Filed: Feb. 5, 1987
[51] Int. Cl.[4] .............................................. A61B 17/20
[52] U.S. Cl. ................................. 604/22; 128/24 A; 128/305; 604/272
[58] Field of Search ............... 128/24 A, 305; 604/19, 604/22, 27, 35, 264, 272, 274

[56] References Cited

U.S. PATENT DOCUMENTS

| | | | |
|---|---|---|---|
| 2,521,161 | 9/1950 | Grover | 128/305 |
| 3,589,363 | 6/1971 | Bonko et al. | 604/22 |
| 3,772,538 | 11/1973 | Supitilov | 310/325 |
| 3,823,717 | 7/1974 | Pohlman et al. | 604/22 |
| 3,896,811 | 7/1975 | Storz | 128/24 A |
| 3,980,906 | 9/1976 | Kuris et al. | 128/24 A |
| 4,169,984 | 10/1979 | Parisi | 128/24 A |
| 4,188,952 | 2/1980 | Loschilov et al. | 128/305 |
| 4,428,748 | 1/1984 | Peyman et al. | 604/22 |
| 4,528,979 | 7/1985 | Marchenko et al. | 128/303.1 |
| 4,531,934 | 7/1985 | Kossovsky et al. | 128/305 |
| 4,561,438 | 12/1985 | Bonnet et al. | 128/24 A |
| 4,689,040 | 8/1987 | Thompson | 604/272 |
| 4,741,731 | 5/1988 | Starck et al. | 604/22 |

FOREIGN PATENT DOCUMENTS

| | | | |
|---|---|---|---|
| 0984770 | 1/1983 | U.S.S.R. | 128/305 |
| 1055501 | 11/1983 | U.S.S.R. | 128/305 |
| 1115740 | 9/1984 | U.S.S.R. | 128/305 |

Primary Examiner—C. Fred Rosenbaum
Assistant Examiner—Mario Costantino
Attorney, Agent, or Firm—Nydegger & Harshman

[57] ABSTRACT

Crystals are energized to vibrate at an ultrasonic frequency. The crystals are coupled to an insert having a body portion coaxial with the crystals so as to vibrate the insert at the ultrasonic frequency. At least one sharp cutting edge extends from one end of the body portion of the insert. The thickness of the insert may taper progressively from the body portion to the sharp cutting edge. The sharp cutting edge may actually constitute a pair of edges disposed in a scissor relationship. The cutting edge(s) may progressively converge to a sharp point. Alternately, the sharp cutting edge may be disposed at the inner periphery of an aperture. Instead of being vibrated at a single ultrasonic frequency, the insert may be vibrated at a pair of ultrasonic frequencies to impart a vibration of the insert simultaneously in the coaxial direction and in a direction perpendicular to the coaxial direction. The insert engages a meniscus to trim fragments from the meniscus. The fragments may be removed from the area of the meniscus by an aspirator which may be disposed in coaxial and enveloping relationship with the insert. The aspirator also acts to pull the partially removed fragments from the meniscus, thereby facilitating the continued operation of the sharp cutting edge(s) in removing the fragment from the meniscus.

6 Claims, 3 Drawing Sheets

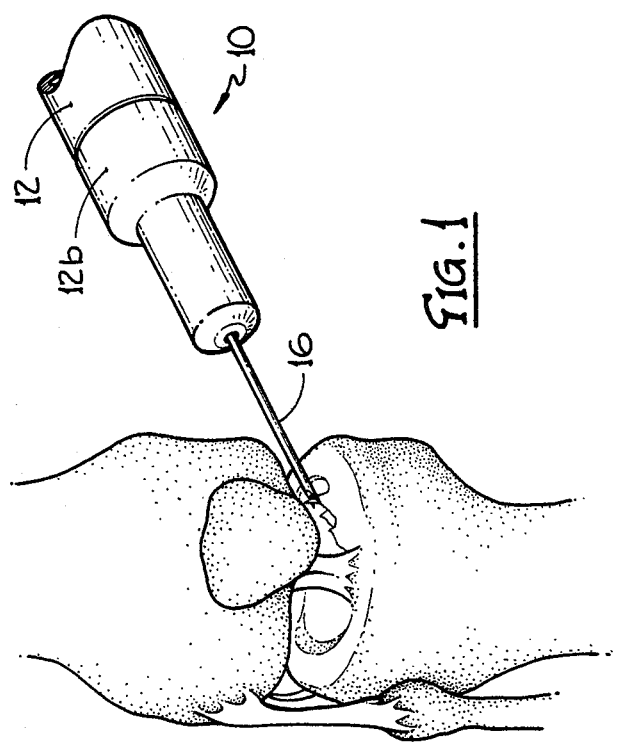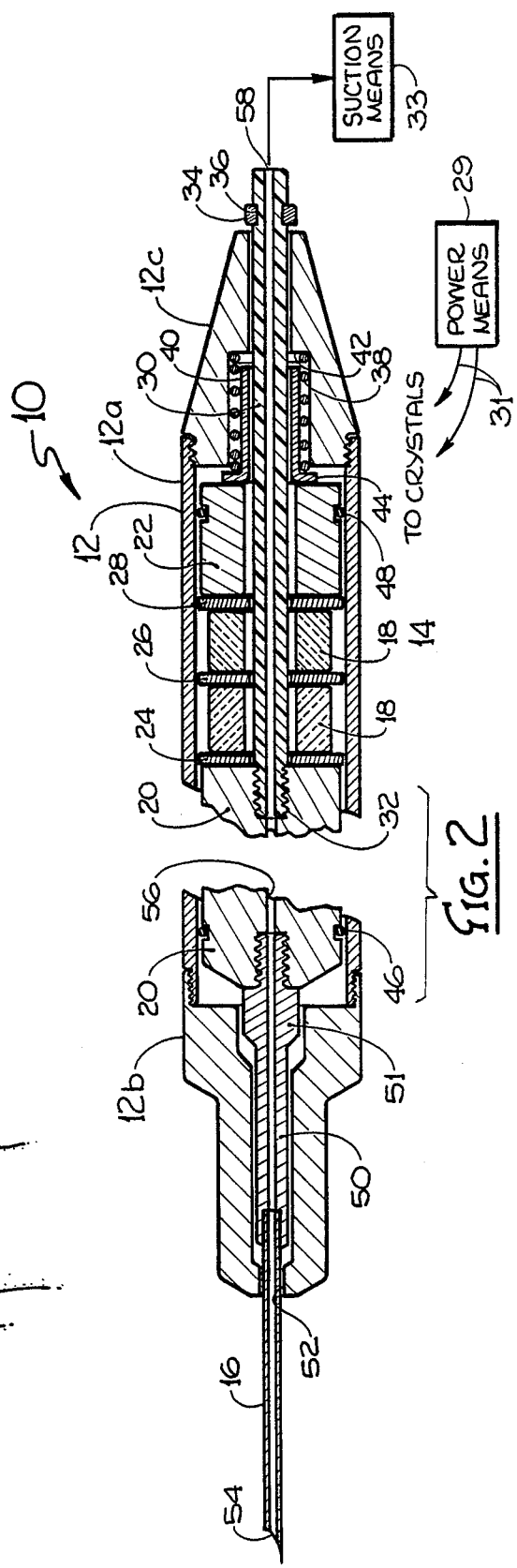

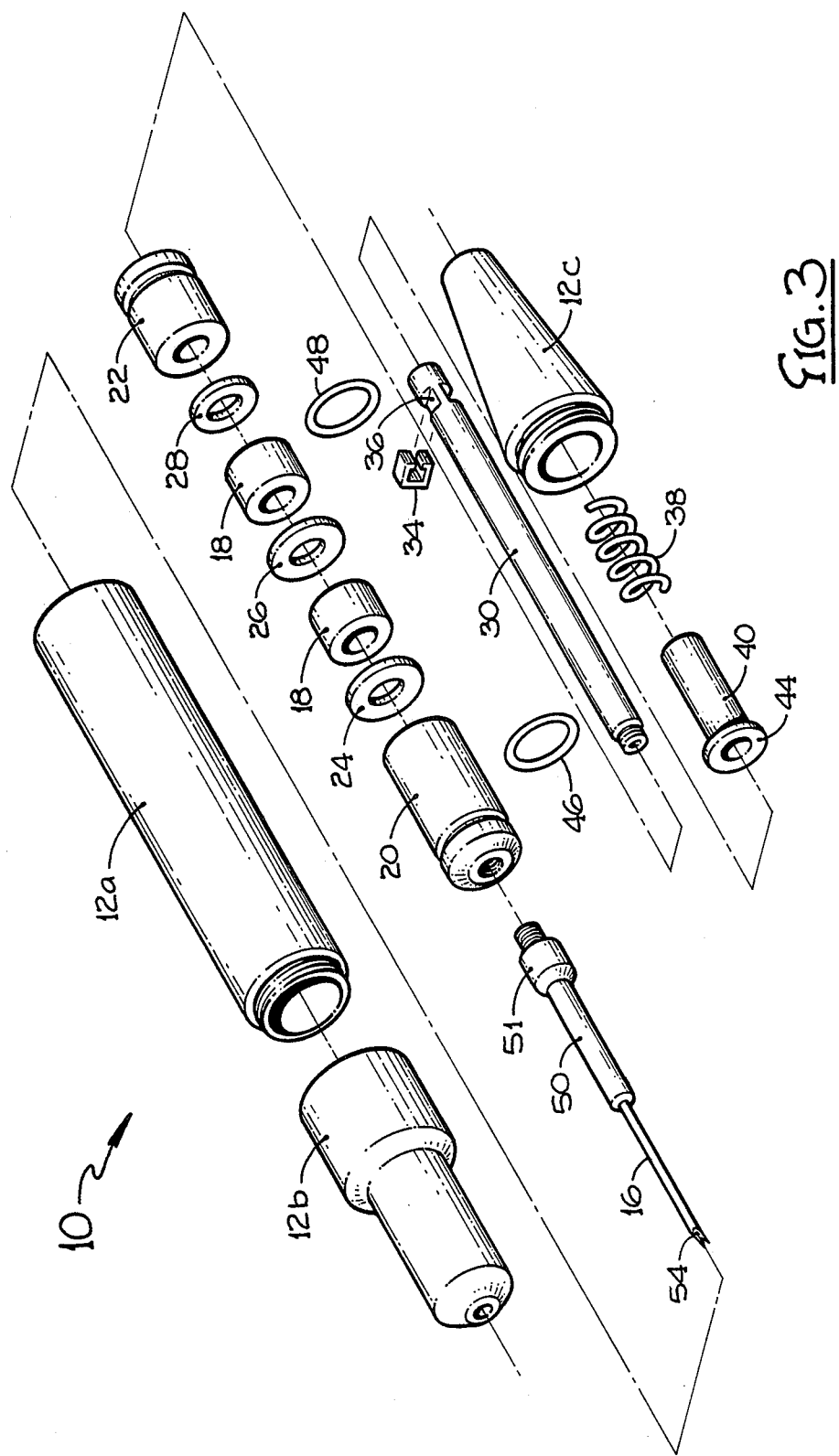

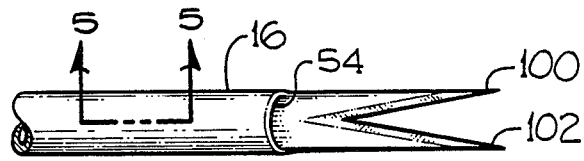
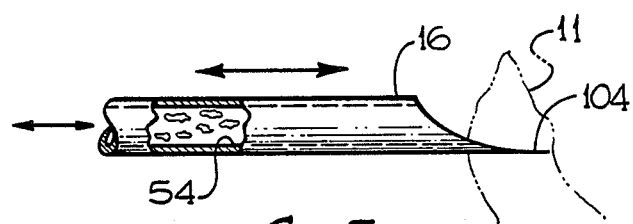
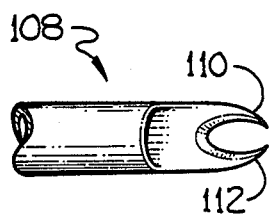 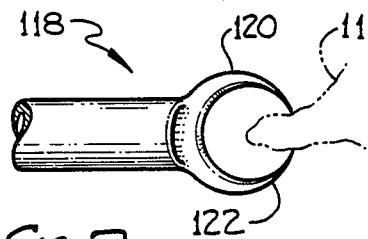
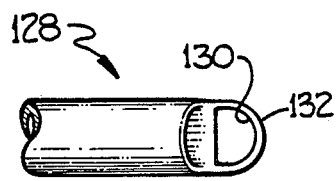 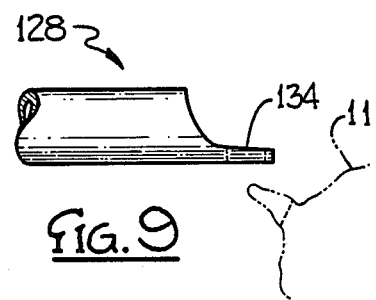

APPARATUS FOR TRIMMING MENISCUS

This invention relates to apparatus for trimming a meniscus in the knee of a human patient. More particularly, this invention relates to apparatus for providing a more efficient and reliable trimming of a meniscus in the knee of a human patient than has accomplished in the prior art.

As people have become increasingly health conscious, they have tended to engage in various forms of athletics in an attempt to maintain their body in good shape. For example, many people now run on a regular basis, some even for long distances. This may be seen from the thousands of people who participate in the various marathon races. Others engage in sports such as tennis and racketball.

In a number of different athletic activities in which health-conscious individuals now engage, the knees of the individuals receive a considerable pounding and wrenching. This results partly from the large forces to which the knees are subjected when the body of the individual contacts the ground. It also results from irregularities in the ground being traversed by the individual. It further results from the unnatural composition of terrain such as concrete or asphalt or artificial turf.

The conditions discussed in the previous paragraph cause the knees of individuals to receive a considerable pounding. This pounding tends to be concentrated at the meniscus which is the tendon allowing the lower part of the leg to flex relative to the thigh. The meniscus accordingly tends to tear or become frayed. This weakens the meniscus so that, unless the meniscus is properly repaired, the meniscus can become further damaged relatively easily.

Various methods and instruments have been devised for repairing a damaged meniscus. Although such methods and instruments have been somewhat effective, they have certain inherent and serious disadvantages. They require more than one person to be present at an operation to repair a meniscus. For example, they require a surgeon to operate on the meniscus and another person to assist in the operation by aspirating fragments cut by the surgeon from the meniscus. This has tended to make the operation on the meniscus awkward and has prevented option results from sometimes being attained.

This invention provides apparatus which overcomes the above difficulties. The apparatus can be handled entirely by the surgeon. Furthermore, the surgeon has only to be concerned by the positioning of the cutting edge relative to the meniscus since the aspirator is coaxial with the cutting edge. In this way, the meniscus can be trimmed with more precision, in a shorter time and with less discomfort to the patient than in the prior art.

In one embodiment of the invention, crystals are energized to vibrate at an ultrasonic frequency. The crystals are coupled to an insert having a body portion coaxial with the crystals so as to vibrate the insert at the ultrasonic frequency. At least one sharp cutting edge extends from one end of the body portion of the insert. The thickness of the insert may taper progressively from the body portion to the sharp cutting edge.

The sharp cutting edge may actually constitute a pair of edges disposed in a scissor relationship. The cutting edge(s) may progressively converge to a sharp point, alternately, the sharp cutting edge may be disposed at the inner periphery of an aperture. Instead of being vibrated at a single ultrasonic frequency, the insert may be vibrated at a pair of ultrasonic frequencies to impart a vibration of the insert simultaneously in the coaxial direction and in a direction perpendicular to the coaxial direction.

The insert engages a meniscus to trim fragments from the meniscus. The fragments may be removed from the area of the meniscus by an aspirator which may be disposed in coaxial and enveloping relationship with the insert. The aspirator also acts to pull partially removed fragments from the meniscus, thereby facilitating the continued operation of the sharp cutting edge(s) in removing the fragment from the meniscus.

In the drawings:

FIG. 1 is a perspective view of an ultrasonic probe including an insert constituting one embodiment of the present invention and shows the probe when applied to a meniscus of a patient;

FIG. 2 is a cross-sectional side view of the probe when taken through the center of the probe;

FIG. 3 is an exploded perspective view of the probe; and

FIG. 4 is an enlarged side elevational view of the insert shown in the previous Figures;

FIG. 5 is a top plan view, broken away to show additional details in section, of the insert shown in the previous Figures and schematically illustrates the operation of the insert in trimming a patient's meniscus;

FIG. 6 is a side elevational view of an insert constituting a second embodiment of the invention;

FIG. 7 is a side elevational view of an insert constituting a third embodiment of the invention;

FIG. 8 is a side elevational view of an insert constituting a fourth embodiment of the invention; and FIG. 9 is a top plan view of the embodiment of the insert shown in FIG. 8.

Reference is now made to the embodiment shows in FIG. 1-5, this embodiment constituting an improved ultrasonic probe, generally indicated at 10, for trimming a meniscus 11 (shown in broken lines in FIG. 5) of a patient. The probe 10 includes a housing, generally indicated at 12, containing a piezoelectric transducer assembly, generally indicated at 14, for imparting ultrasonic vibrations to an elongated operative insert 16. The housing 12 includes a central cylindrical member 12a and a pair of end members 12b and 12c.

Referring to FIGS. 2 and 3, piezoelectric transducer assembly 14 includes first and second piezoelectric crystals 18 located within the housing 12 between a first body member 20 and a second body member 22. The piezoelectric crystals 18 are powered through disc electrodes 24, 26 and 28 connected to a high frequency source or power means 29 of alternating current by lead wires 31. The disc electrode 26 is positioned between the crystals 18 and 20 and the electrodes 26 and 28 are positioned between the crystals and the body members 20 and 22, respectively.

A connecting tube 30 extends through axial bores in the crystals 18, body members 20 and 22 and electrodes 24, 26 and 28 to maintain these components in axial alignment within the housing 12. A forward end of the connecting tube 30 includes threads 32 that engage threads in the axial bore of the first body member 20 for secure connection. The rear end of the tube 30 extends through the end member 12c of the housing 12 for connection to a suction source 33. A clip 34 received in a detent 36 in the connecting tube 30 abuts the end member 12c and allows the prestressing of the crystals 18 as discussed in further detail below.

A coil spring 38 provides for a resilient compression to the crystals 18 so as to assure a consistent and reliable operation of the probe under all operating conditions. The spring 38 is disposed around, and carried on, a guide sleeve 40 that maintains the spring in proper position within the end member 12c of the housing 12. The coil spring 38 is compressed between a wall 42 of the end member 12c and a collar 44 of the guide sleeve 40. The coil spring 38 also acts to store energy during the vibratory movement of the piezoelectric crystals toward the right in FIG. 3 and to urge the crystals toward the left in FIG. 2 when the crystals start to vibrate toward the left in FIG. 2. This tends to amplify the ultrasonic vibrations imparted to the insert 16 by the crystals 18. Since the connecting tube 30 is secured to the first body member 20 by the threads 32 and anchored adjacent its distal end by the clip 34 abutting the end member 12c, it should be appreciated that the crystals 18 are prestressed between the body members 20 and 22.

The force thus generated by the coil spring 38 provides a substantially constant and uniform loading across the crystals 18, substantially eliminating localized stresses that can result in crystal breakage. Further, the resilient nature of the compression provided to the crystals 18 by the spring 38 dramatically increases electromechanical coupling over the rigid nature of the compression provided by the bolting together of the crystals as done in the prior art. The probe 10 of the present invention is therefore more efficient than the probes of the prior art, allowing effective operation at a lower voltage with reduced dielectric losses. Thus, the probe operates at a lower overall temperature than the probes of the prior art, thereby reducing cooling requirements and improving reliability.

The body members 20 and 22 are electrically and mechanically insulated from the housing 12 by O-rings 46 and 48. The O-rings 46 and 48 float the body members 20 and 22 within the housing 12 so that the ultrasonic vibrations are not coupled to the housing. Since the housing 12 does not receive any ultrasonic vibrations, it can be handled more easily and with more precision than the housings of the prior art.

An alternating voltage is applied across the piezoelectric transducers 18 between the disc electrodes 24, 26 and 28, causing piezoelectric the crystals 18 to vibrate at an ultrasonic frequency. Ultrasonic vibrations are imparted by the crystals 18 to the insert 16 by mechanical coupling through the disc electrode 25, the first body member 20 and an enlarged tip base 50 in the insert 16.

A portion of the insert 16, including the base 50 is contained within the housing 12. The base 50 has an increased mass 51 at one end. The mass 51 stores energy and uses this energy as a hammer to increase the force imposed upon the insert 16 when the insert is moved to the left in FIG. 2 by the crystal transducers 18. In this way, the mass 51 acts to amplify the ultrasonic vibrations imparted to the insert 16.

The remaining portion of the insert 16 extends beyond the housing 12 through an aperture 52 at one end of the housing member 12b. The insert 16 contains an inner passageway 54 for aspiration of removed material. The inner passageway 54 is aligned in communication with an axial bore 56 of the first body member 20 and an inner passage 58 of the connecting tube 30 to form a substantially straight-through aspiration path.

When the operative tip 16 vibrates at an ultrasonic frequency, it operates to trim a meniscus indicated in broken lines at 104 in FIG. 5. The trimmed fragments of the meniscus aspirated through the inner passages 54, 56 and 58 of the insert 16, the first body member 20 and the connecting tube 30, respectively, to the suction source 33.

As will be seen, the ultrasonic probe 10 of the present invention provides a uniform and constant prestress compression loading of the piezoelectric transducer 18 and provides a substantially straight-through aspiration through the insert 16. These provide significant advantages over the ultrasonic probes of the prior art. The resilient coil spring 30 provides a uniform compression loading which avoids breakage of the transducers such as the insert 16 during mounting or operation of the transducers. Enhanced electromechanical coupling is also provided for improved operating efficiency at reduced temperatures. The spring 30 also acts to amplify the ultrasonic vibrations of the insert 16. The mass 51 on the base 50 also acts to amplify the ultrasonic vibrations of the insert 16.

The construction of the insert 16 is further shown in FIGS. 4 and 5. As shown in FIGS. 4 and 5, the insert 16 preferably has a pair of cutting elements 100 and 102 disposed in a scissors-type of arrangement. Each of the cutting elements 100 and 102 tapers in the vertical direction with progressive distances toward the cutting edges of the elements. The cutting elements 100 and 102 also taper in the horizontal direction with progressive distances toward the cutting edges of the elements. Although two cutting elements are shown in FIGS. 4 and 5, it will be appreciated that an insert with only a single cutting element is also within the scope of the invention. However, the use of the two cutting elements 100 and 102 are advantageous because they act as a pincer in trimming the meniscus.

As the cutting elements 100 and 102 trim the meniscus, the trimmed fragments of the meniscus are separated from the remainder of the meniscus to which the trimmed fragment is attached. This separation is provided because of the vacuum force produced through the passages 54, 56 and 58. Because of this separation between the portion of the meniscus being trimmed and the attached portion of the meniscus, the continued trimming of the fragment from the remainder of the meniscus is facilitated. This results from the fact that the cutting elements 100 and 102 experience only a minimal friction from the trimmed portion of the meniscus.

The cutting edges of the elements 100 and 102 tend to become heated by the application of the ultrasonic energy to such edges and by even the minimal friction between such edges and the meniscus as the fragments are being trimmed from the meniscus. The heat produced at the cutting edges of the elements 100 and 102 tends to soften the meniscus at the surface being trimmed so that the trimming of the meniscus is facilitated.

Although the insert 16 trims fragments of the meniscus effectively, the insert 16 does not damage blood vessels. This results from the fact that the cutting elements 100 and 102 of the insert 16 tend to glide over the blood vessels. This may result from the fact that the blood vessels may be resilient. Damaging of the blood vessels is undesirable for two reasons. One reason is that the patient is injured, sometimes seriously. Another reason is that the flow of blood impedes the ability of the surgeon to trim the meniscus effectively since it obscures the view of the patient in providing such trimming.

Instead of introducing ultrasonic energy to the insert 16 at a single frequency in the range of approximately forty (40) to sixty (60) kilohertz (KHz), the power means 28 may introduce ultrasonic energy to the insert at a combination of frequencies. The mixing of these frequencies tends to produce jolts in the actuation of the insert. These jolts tend to cause the insert 16 to vibrate with a component vertical to the length of the insert as well as along the length of the insert. The vibration of the insert 16 with a vertical component is sometimes desirable because it helps the insert 16 to move around corners. This facilitates the trimming of the meniscus 100 by the insert 16.

FIG. 6 illustrates another embodiment of the insert 16. In the embodiment shown in FIG. 6, an insert 108 is provided with a pair of elements 110 and 112 which define a pincers arrangement. The pincers elements 110 and 112 preferably have a curved configuration relative to each other whereby the elements slope toward each other at their cutting edges. This facilitates the ability of the insert 108 to be rotated in the plane of the inserts to facilitate the positioning of the insert relative to the meniscus in a direction perpendicular to the direction of the ultrasonic vibrations of the crystals 18. This enhances the ability of the insert 108 to trim the meniscus. FIG. 7 illustrates an embodiment of an insert 118, having elements 120 and 122 with a curvature even more pronounced than the curvature of the elements 110 and 112 in the embodiment shown in FIG. 6.

FIGS. 8 and 9 illustrate another embodiment of the invention. In this embodiment, an insert 128 is provided with an aperture 130 which defines a cutting edge 132. The tip of the insert 128 is progressively tapered as at 134 to the portion in which the aperture 130 and the cutting edge 132 are provided. The taper 134 enhances the ability of the insert 128 to withstand, without fatiguing, the forces to which the insert 128 is subjected when it is vibrated at the ultrasonic frequencies. The taper 134 also facilitates the introduction of the ultrasonic energy to the cutting edge 132. In the embodiment shown in FIGS. 8 and 9, the insert 128 is positioned so that the portion of a meniscus 136 to be trimmed is disposed in the aperture 130. The trimming is then provided by the cutting edge 132.

Although this invention has been disclosed and illustrated with reference to particular embodiments, the principles involved are susceptible for use in numerous other embodiments which will be apparent to persons skilled in the art. The invention is, therefore, to be limited only as indicated by the scope of the appended claims.

I claim:

1. In combination for trimming a meniscus,
means for providing a vacuum,
means for providing energy at a particular ultrasonic frequency,
the vacuum means being coaxial with the ultrasonic energy means,
an insert operatively coupled to the ultrasonic energy means coaxially with the ultrasonic energy means and communicating with the vacuum means to introduce the ultrasonic energy to the insert to vibrate the insert at the ultrasonic frequency at the position of the meniscus and to provide for the removal by the vacuum means of cut fragments of the meniscus,
the insert being provided with two sharp edges in spaced relationship to each other, the two sharp edges being separated by an indented portion, each of the sharp edges being provided with a tapered thickness extending to the sharp edge,
the operative coupling between the insert and the energy means being provided by a pair of body members disposed at opposite ends of the energy means,
a housing,
a connecting tube coupled at its opposite ends to the housing and to the body member closest to the insert,
the connecting tube, the energy means and the body members being disposed within the housing, and
the insert, the housing, the connecting tube, the energy means and the body members being provided with axial opening communicating with one another to provide for the axial introduction of the vacuum from the vacuum means to the sharp edge of the insert.

2. In combination for trimming a meniscus,
an insert having an axially extending body portion and having two sharp edges separated by an indented portion, each of the sharp edges being provided with a tapered thickness extending to the sharp edge at the end of the body portion, the insert having a thickness tapering progressively from the body portion to the cutting edge, the insert having an axial opening and provided with an aperture at the end of the body portion and the sharp edge being provided at the aperture in the insert,
means for providing energy at an ultrasonic frequency, the energy means being axially aligned with the insert and being coupled to the insert to drive the insert at the ultrasonic frequency, the energy means being provided with an axial opening,
means for pressing the body members against the energy means,
means disposed in axially aligned relationship with the insert for aspirating the fragments cut by the insert from the meniscus and being operative on the fragment being cut from the meniscus to separate such fragment from the remainder of the meniscus, the aspirating means including a pair of body members disposed on opposite sides of the energy means and being provided with an axial opening,
a connecting tube having an axial opening and disposed in the axial openings in the body members and the energy means and constructed to cooperate with the pressing means to retain the energy means and the body members in fixed relationship to one another, and
the axial openings in the insert, the energy means and the aspirating means communicating with one another.

3. In combination for trimming a meniscus,
an insert having an axially extending body portion and having a pair of sharp cutting edges at the end of the body portion, the insert having a thickness extending progressively from the body portion to the sharp cutting edges, the sharp cutting edges being separated by an indented portion, each of the sharp edges being provided with a tapered thickness extending to the sharp edge,
means disposed in coaxial relationship with the insert for vibrating the insert in the axial direction at an ultrasonic frequency, and means disposed in coaxial relationship with the insert for aspirating the fragments removed from the meniscus by the vibration of the insert at the ultrasonic frequency, the aspirating means including a pair of body members disposed at opposite ends of the vibrating means, the vibrating mean, the insert and the aspirating means including the body members being provided with axial openings communicating with one another, and the aspirating means also including a connecting tube extending through the axial openings in the body members and the vibrating means and operatively coupled to one of the body members to retain the body members and the vibrating means in a fixed relationship to one another, the connecting tube being provided with an axial opening communicating with the axial openings in the insert, the vibrating means and the aspirating means.

4. In a combination as set forth in claim 3, the insert being tapered progressively from the body portion to the sharp cutting edges, a housing for holding the insert, the vibrating means and the aspirating means, and means associated with the housing and co-operating with the connecting tube to hold the vibrating means and the body members in abutting relationship.

5. In a combination as set forth in claim 4, the sharp cutting edges being shaped to define sharp points, and a spring axially disposed within the housing in abutting relationship to one of the body members to enhance the vibrations of the insert.

6. In a combination as set forth in claim 4, the sharp cutting edges being bent to point toward each other.

* * * * *